United States Patent [19]

Kurata et al.

[11] Patent Number: 5,456,916
[45] Date of Patent: Oct. 10, 1995

[54] MICROCAPSULES CONTAINING CAPSAICINE COMPOUND AND THEIR PRODUCTION

[75] Inventors: Mitsuo Kurata, Ageo; Yasuhiro Ichikawa; Mika Toya, both of Yono; Iwao Takahashi, Omiya; Yoshinobu Okui, Koga; Shoichi Kato, Ageo; Takeshi Nishitani, Urawa, all of Japan

[73] Assignee: Nippon Kayaku Kabushiki Kaisha, Tokyo, Japan

[21] Appl. No.: 199,860

[22] Filed: Feb. 22, 1994

Related U.S. Application Data

[60] Division of Ser. No. 931,057, Aug. 17, 1992, Pat. No. 5,322,862, which is a continuation-in-part of Ser. No. 700,536, May 14, 1991, abandoned.

[30] Foreign Application Priority Data

May 22, 1990 [JP] Japan ..................... 2-130209
Jun. 1, 1990 [JP] Japan ..................... 2-141538
Jan. 17, 1991 [JP] Japan ..................... 3-15638

[51] Int. Cl.$^6$ .................... A01N 25/34; B01J 13/16; B01J 13/18; C08K 5/20
[52] U.S. Cl. ................... 424/408; 264/4.7; 424/419; 428/402.21; 514/627; 514/920; 514/962
[58] Field of Search ................ 264/4.7; 428/402.21, 428/402.22; 514/627, 920, 962; 424/408, 419

[56] References Cited

U.S. PATENT DOCUMENTS

| | | | |
|---|---|---|---|
| 3,577,515 | 5/1971 | Vandegaer | 264/4.7 X |
| 4,097,607 | 6/1978 | Larson | 514/627 |
| 4,140,516 | 2/1979 | Scher | 264/4.7 X |
| 4,179,499 | 12/1979 | Christensen | 514/627 |
| 4,193,889 | 3/1980 | Baatz et al. | 264/4.7 X |
| 4,532,189 | 7/1985 | Janusz et al. | 514/627 |
| 4,680,313 | 7/1987 | Iwai | 514/627 |
| 4,789,687 | 12/1988 | Iwai | 514/627 |
| 4,900,551 | 2/1990 | Ohtsubo et al. | 424/408 |
| 4,915,947 | 4/1990 | Thenard et al. | 424/408 |
| 4,917,920 | 4/1990 | Ono et al. | 427/389.9 |
| 5,002,768 | 3/1991 | Kondo et al. | 424/408 |
| 5,039,524 | 8/1991 | Oishi et al. | 424/408 |
| 5,322,862 | 6/1994 | Kurata et al. | 424/408 X |

FOREIGN PATENT DOCUMENTS

| | | |
|---|---|---|
| 2217396 | 9/1974 | France . |
| 2340626 | 8/1974 | Germany . |
| 49-112932 | 10/1974 | Japan . |
| 61-155325 | 7/1986 | Japan . |
| 595766 | 2/1978 | Switzerland . |

OTHER PUBLICATIONS

Chemical Patents Index, Documentation Abstracts Journal, C Agrochemicals, week 8843, 21st Dec. 1988, accession no. 88-3048 99/43, Derwent Publications Ltd., London. GB:& JP-A-63 225 643 (Dainichi Nippon Cables) 20-09-1988.
Chemical Patents Index, Documentation Abstracts Journal, C Agrochemicals, week 8843, 21st Dec. 1988, accession no. 88-3049 15/43, Derwent Publications Ltd.: London, GB:& JP-A-63 225 672 (Dainichi Nippon Cable) 20-09-1988.

*Primary Examiner*—Richard D. Lovering
*Attorney, Agent, or Firm*—Nields & Lemack

[57] ABSTRACT

The present invention provides a resin molding composition for preventing gnawing damage by the animal, a microcapsule filled with a capsaicine compound, and a process for producing the capsaicine compound and the microcapsule.

4 Claims, No Drawings

MICROCAPSULES CONTAINING CAPSAICINE COMPOUND AND THEIR PRODUCTION

This application is a division of U.S. application Ser. No. 07/931,057 filed Aug. 17, 1992, U.S. Pat. No. 5,322,862, which is continuation-in-part of U.S. application Ser. No. 07/700,536 filed May 14, 1991, now abandoned.

DETAILED DESCRIPTION OF THE INVENTION

The present invention relates to a resin molding composition having an ability to prevent "gnawing damage", or damage caused by gnawing or biting by the animals, microcapsules used for the above object and process for producing the microcapsules. The composition is used for preventing such gnawing damage by rodents and other animals on the resin-molded articles and wood used for a variety of applications such as covering of the cables for power transmission, communication, transfer of signals, etc., packages, equipments, apparatuses, building structures, etc.

Various kinds of repellents have been proposed as one of effective means for preventing rodents and other animals from damage to the agricultural and forestry industries, entering into the office buildings, apartments, houses, food storehouses, factories, electric installations and arrangements, communication facilities, etc., and gnawing the packages, electric wires, telephone lines, signal and communication cables, computer equipment, etc., and some of such repellents are in practical use. For instance, cycloheximide, ZAC (zinc dimethyl dithiocarbamate and cyclohexylamine complex) and trialkyltin compounds are known as the repellents to be applied on the natural and synthetic resin products, and cycloheximide, ZAC and R-55 (tertiary butylsulphenyl dithiocarbamate) can be mentioned as the repellents that can be mixed with resins.

Especially, cycloheximide, which is an antibiotic discovered in 1950, is widely used for its excellent preventive effect against gnawing damage by rodents and other animals, but this substance is expensive as it is an antibiotic. Also, this substance is relatively high in toxicity and almost tasteless to men, so that there are certain restrictions in its practical use because of safety problem, for example, danger that an infant may lick a domestic electric cord treated with said substance. Cycloheximide is also highly soluble in water and easily decomposed at high temperatures, so that, in practical use, it is made into microcapsules for minimizing its harmful influence and such microcapsules are incorporated into the articles such as the sheath of electric wires.

In view of the fact that said cycloheximide has on one hand a prominent effect for preventing gnawing damage by rodents and other animals but on the other hand it is expensive, relatively high in toxicity, almost tasteless to men and apt to be influenced by various environmental factors and in the preparation process because of high water solubility and readiness to decompose at high temperatures, the present inventors have ardently pursued the studies aimed at developing a more useful and safe version of said substance that can be used in the wide fields such as mentioned above and a method for producing such improved version of said substance, and as a result, the present inventors took notice of capsaicines which are a pungent component of capsicum which exists in nature, found that this substance could answer said purpose, and achieved the present invention based on said finding.

In the past, attempts have been made of using a capsicum extract, in a liquid form, as a repellent for protecting the plants from field mice, hares and other feral herbivorous animals, or of mixing a capsaicine compound in a paint and coating an object with such mixed paint for preventing lead poisoning that could otherwise be caused when a child gnawed or licked the object coated with a lead-containing paint (Japanese Patent Application Kokai (Laid-Open) No. 112932/1974).

Generally, in case of using capsaicine compounds for preventing gnawing damage by rodents and other animals to the plastic moldings and wood, which is the object of this invention, when said substance is mixed in a paint and the mixed paint is used for surface treatment, the formed coating film is too thin and unable to maintain the substance activity for a long time because of exfoliation or other causes, and when said substance is prepared into a liquid agent and sprayed for said purpose, it is not only difficult to maintain the effect for a long time but the applied liquid may also adhere to the worker's clothing as well as his hands and feet to remain as a pungent remnant. Also, this substance has a strong stimulus and is therefore hard to handle, which has been another negative factor for practical use of said substance.

Therefore, for example, there is a literature which describes that the synthesis of capsaicines was carried out in a completely closed system (Hiroo Ueda, Perfumes No. 129, 41–46, October, 1980). However, the finding of a method enabling more safe and effective use of said substance, for example, not only during synthesis but also in many steps such as taking out of the synthesized capsaicine compound, weighing and packing it, has been desired.

In the efforts for solving said problems, the present inventors focused on the fact that although the capsaicine compounds have a strong pungent taste and stimulus and are hard to treat, they have excellent repellency to the animals, exist in foods, are hardly gasified and decomposed at the temperatures below 200° C. at which resins are generally molded, have relatively good compatibility with resins and plasticizers, and are hardly or only sparingly soluble in water so that they can be easily subjected to resin working and are scarcely influenced by the various environmental factors. And as a result of further studies with these facts in mind, the present inventors found that by microencapsulating the capsaicine compound, the strong pungency and stimulus of the capsaicine compounds can be prevented from contamination due to transferring, etc., i.e. can be properly covered up by containing said microcapsules filled with the compound in a resin, and that they have sufficient feasibility for use for preventing gnawing damage by the animals such as rodents, dogs, cats and other wild animals. These findings have led to the attainment of the present invention.

Furthermore, the present inventors have succeeded in producing microcapsules of the capsaicine compounds having a weak pungent nature in one bath without the need for direct contact with the crude capsaicine compounds having a strong irritant nature by preparing the capsaicine compounds from a starting material having a weak irritant nature and charging a starting material for microencapsulation into the same reaction vessel.

The present invention will be described in detail below.

The present invention provides a resin molding composition for preventing gnawing damage by the animals characterized in that the composition contains microcapsules of a capsaicine compound represented by the following formula (1):

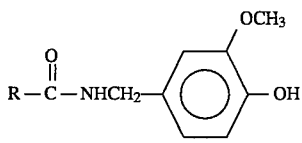

(1)

wherein R represents an alkyl, alkynyl or alkenyl group, each group has 7 to 12 carbon atoms.

The present invention further provides a microcapsule filled with the capsaicine compound as defined above.

The present invention still further provides a process for producing the capsaicine compound and the microcapsule.

Among the capsaicine compounds represented by the formula (1), those in which R in the formula (1) has 7 to 10 carbon atoms are preferred. Some examples are shown below:

R=$CH_3(CH_2)_6$ (caprylic acid vanillylamide),
R=$CH_3(CH_2)_7$ (nonylic acid vanillylamide),
R=$CH_3(CH_2)_8$ (decylic acid vanillylamide),
R=$(CH_3)_2CH(CH_2)_5$ (nordihydrocapsaicine I),
R=$(CH_3)_2CH(CH_2)_6$ (dihydrocapsaicine),
R=$(CH_3)_2CH(CH_2)_7$ (homodihydrocapsaicine I),
R=$CH_3CH_2CH(CH_3)(CH_2)_4$ (nordihydrocapsaicine II),
R=$CH_3CH_2CH(CH_3)(CH_2)_6$ (homodihydrocapsaicine II),
R=$(CH_3)_2CHCH=CH(CH_2)_4$ (capsaicine),
R=$(CH_3)_2CHCH_2CH=CH(CH_2)_4$ (homocapsaicine I), and
R=$CH_3CH_2CH(CH_3)CH=CH (CH_2)_4$ (homocapsaicine II).

Some capsaicine compounds of the formula (1) can also be extracted from capsicum. The capsicum extract can be obtained in the following way.

Dried and pulverized capsicum is extracted with an alcohol type solvent such as methanol and ethanol, an ether type solvent such as ethyl ether, a ketone type solvent such as acetone, an aromatic solvent such as benzene, a chlorine type solvent such as dichloroethane and chloroform, or other suitable types of solvent, and after filtration, the filtrate is heated in an evaporator under reduced pressure to remove the solvent to obtain a capsicum extract. This extract may be chromatographed by using silica gel or alumina column to obtain a capsicum extract containing capsaicine compounds in a higher concentration.

The effective concentration of the capsaicine compound used in the present invention is usually 0.01 to 10%, preferably 0.1 to 5%, based on the whole amount of the resin molding composition. Such concentration may be properly decided within the above range in view of efficacy and economy by also giving consideration to the various restrictive conditions according to the form of use. Known methods can be employed for incorporating microcapsules filled with the capsaicine compound in resin. For example, may be mentioned a method in which the microcapsules are directly added to and mixed with the resin material and adjuvants such as plasticizer, pigment, etc., and the mixture is molded, or a method in which a master batch containing the capsaicine compound in a high concentration is prepared in advance and this master batch is diluted with other resin material(s) to a desired concentration when molding is conducted.

The advantage that the capsaicine compound is microencapsulated and the microcapsules are incorporated in resin by a method such as mentioned above are as follows. Generally, the capsaicine compounds, when heated with a thermoplastic resin and other materials for molding, generate a strongly stimulative gaseous substance although very small in amount, so that it is required to take a prudent measure at the manufacturing place but the microencapsulated capsaicine compounds can eliminate such problem.

Thus, pungency remaining slightly on the molded resin surface was suppressed to facilitate handling of the capsaicine-containing resin molded articles, and yet it was confirmed that the effect of preventing gnawing damage by rodents and other animals was not reduced but rather raised significantly. This can be accounted for by the fact that when an animal such as a rodent gnaws the object (capsaicine-incorporated resin molded article), the capsule walls are broken and the high-concentration capsaicine compound runs out of the broken capsules to give a biting stimulus to the animal. Thus, said substance can act more effectively in this way.

The encapsulation techniques usable in the present invention are not restricted and it is possible to employ various known techniques. For example, may be mentioned a method making use of interfacial polymerization techniques according to which a raw wall material is dissolved in the core material containing a capsaicine compound to be microencapsulated, then this solution is dispersed in an insoluble dispersing medium (usually water), and then a proper reactant soluble in the dispersing medium is added to the dispersion with stirring to allow said materials react on the dispersed particle surfaces to form the capsule walls encapsulating the core material, or a method making use of in-situ polymerization techniques in which the capsule walls are formed on the dispersed particle surfaces with the wall material being supplied from either dispersed particles or dispersing medium. Other known encapsulation techniques such as coacervation, in-air-phase microencapsulation method, etc., can be used as well.

As wall material for in-liquid microencapsulation, there can be used urea resin, melamine resin, guanamine resin, phenol resin, polyamide, polyurea, polyurethane, polyester, gelatin, etc., which are reacted with a monomer, low-molecular weight prepolymer, crosslinking agent, polymerization initiator or the like. As wall material for in-air-phase encapsulation, there can be used polyvinyl alcohol, polyacrylic acid, cellulose acetate, polymethacrylate and the like. These materials can be used either singly or in combination.

It was found that use of melamine resin as capsule wall material could elevate the repellent effect to the animals. Specifically, microcapsules can be prepared according to the in-situ polymerization techniques by using melamine and formaldehyde or its precondensate (methylolmelamine) as starting materials for the walls in an acidic condition. This method is but an example, and other methods and other wall materials can be properly used as well in conformity to the mode of use, various conditions, economy and other factors.

The microcapsule formulations usable in this invention are prepared in powder form containing usually 1% by weight or more, preferably 5 to 80% by weight of a capsaicine compound. Drying for forming such a powder can be accomplished by various methods such as spray drying, multi-stage hot-air drying, vacuum drying, etc.

The weight ratio of core material in a microcapsule to its wall material may be generally 1:0.01 to 1:10, preferably 1:0.1 to 1:2, but not restricted to the above range.

The mean particle diameter of the microcapsules can be varied as desired, but usually it is adjusted to be in the range of 1 to 150 μm. For maximizing the preventive effect against gnawing damage by the animals, it is preferred that the microcapsules be so prepared that 90% or more of them will have a particle diameter in the range of 5 to 100 μm, with the mean particle diameter being 15 to 50 μm.

The process of microencapsulation, generally, involves two stages of (1) dispersing the capsaicine compound in water and (2) forming the polymer wall around the dispersed particles containing the capsaicine compound. Adjustment of particle size may be affected by viscosity of a core material, temperature for dispersion, an apparatus for dispersion, rotational speed of the agitator acquired by the apparatus, time for dispersion, the kind or amount of the dispersing agent etc. For example, in order to obtain 1 liter of the microcapsule dispersion having the mean particle diameter within the range mentioned above using 1 liter-size mixer (produced by Matsushita Electric Co., Ltd., MX-M2), dispersing may be conducted at 20° to 50° C., at 1000 to 1500 rpm for 5 minutes. And, in order to obtain 1 liter of the microcapsule dispersion having the mean particle diameter within the range mentioned above using 1 liter size round-bottom flask equipped with 7 cm-length brade for stirring, microencapsulating (dispersing) may be conducted at 50° to 85° C., at 500 to 700 rpm for 30 minutes. The rotational speed of forming the polymer wall does not much affect to the particle diameter, if the rotational speed is less than that of dispersion.

In order to obtain the microcapsules of the present invention, any kind of the capsaicine compound of the formula (1) can be used as a core material, that is, the method for producing the compound is not limited to the particular methods. However, it is advantageous if the following method is provided.

Namely, the present invention further provides a process for producing a capsaicine compound and microcapsules thereof comprising the steps of: preparing a capsaicine compound represented by the following general formula (1):

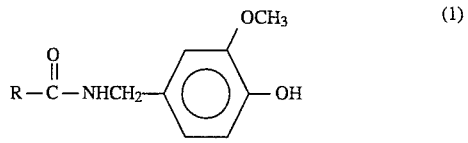

wherein R represents an alkyl group, an alkenyl group or an alkynyl group, each group has 7 to 12 carbon atoms, by condensing a compound represented by the following general formula (2)

wherein R is defined as above and Hal represents a halogen atom and vanillylamine or a salt thereof in a solvent in the presence of an acid binding agent, if necessary; charging a starting material necessary for microencapsulation such as an encapsulating agent in the same reaction bath in this state; and producing the microcapsules by oil-in-water dispersion system. In this way, it is possible to obtain microcapsules of the capsaicine compound which are very safe and easy to handle for the manufacturing workers.

According to the above process, the capsaicine compounds are synthesized in a completely closed system and microencapsulated without being taken out of the system. Since they are produced in the form which enables safe and easy handling, it becomes easier to use the capsaicine compounds in the form of a mixture with various adjuvants or resins, for example, and the long-time time durability of effectiveness which is characteristic of microcapsules are imparted to the capsaicine compound.

In the synthesis of the capsaicine compounds, as the solvent used for condensation reaction, there may be mentioned water, aromatic hydrocarbons such as benzene, toluene and xylene, aliphatic hydrocarbons such as hexane, heptane and petroleum benzine, halogenated hydrocarbons such as chloroform and dichloromethane, ethers such as diethyl ether, tetrahydrofuran and dioxane, and solvents which are mainly used as a plasticizer for resins such as phthalate, adipate, phosphate and maleate. These solvents may be used in the form of a mixture solvent (e.g., solvent of water and benzene).

The acid binding agent is unnecessary when two or more equivalents of vanillylamine is used for the compound represented by the formula (2). In the case of using an equivalent of vanillylamine to the compound of the formula (2), not less than 1 equivalent of the acid binding agent is necessary. In the case of using hydrochloride, hydrobromide or other salt of vanillylamine, not less than two equivalents of at least one acid binding agent is necessary for the salt in order to decompose the salt to liberate vanillylamine and condense vanillylamine with the compound represented by the formula (2) so as to complete the reaction.

As examples of the acid binding agent there may be mentioned alkali metal hydroxide (e.g., NaOH and KOH), alkaline earth metal hydroxide (e.g., $Ca(OH)_2$, $Mg(OH)_2$), alkali metal hydride (e.g., NaH), alkali metal alcoholate (alkoxide) (e.g., $NaOC_2H_5$), alkali metal oxide (e.g., $Na_2O$, $K_2O$), alkali metal carbonate (e.g., $K_2CO_3$, $Na_2CO_3$, etc.) and aliphatic and aromatic tertiary amine such as sodium amide, triethylamine, N,N-dialkylaniline and pyridine. Silver oxide is also usable. It is also possible to use a phase-transfer catalyst represented by tetra-n-butyl ammonium and triethyl benzyl ammonium chloride in the case of bringing about reaction in a two-phase system by mixing water with a water-insoluble solvent.

The above-described condensation is ordinarily carried out at room temperature to the boiling point of the solvent used.

Although some compounds represented by the formula (2) as the starting material are commercially available as a reagent, it is easy to produce a compound represented by the formula (2) by reacting a compound represented by the following general formula (3):

wherein R is defined as above with, for example, excess phosphorus trichloride, thionyl chloride or phosphorus tribromide in a condensation solvent such as that described above, as desired.

Thus, according to the present invention, it is possible to carry out the three steps in one bath, namely, the step of producing a compound represented by the formula (2) from a starting material represented by the formula (3), the step of producing a compound represented by the formula (1) by condensation reaction, and the step of microencapsulating the compound obtained.

After obtaining such a crude capsaicine compound in the solvent in this way, it is microencapsulated in the same reactor without being taken out in accordance with the microencapsulating conditions mentioned above. If necessary, the capsaicine compound is purified before microencapsulation by adding a water-insoluble or -slightly soluble solvent to the crude capsaicine compound in the reaction vessel, stirring the mixture for a predetermined time and then removing the water layer. Alternatively, the residue obtained by distilling off the solvent used for the reaction by vacuum distillation or the like is microencapsulated so as to confine the capsaicine compound having a strong irritant nature in microcapsules and obtain microcapsules of the capsaicine compound having a very weak irritant nature.

Since the steps from the synthesis of the capsaicine compound to microencapsulation of it are carried out in one bath, it is necessary that the reaction vessel used in the present invention has an agitator which rotates variably from a low speed to a high speed, a jacket or an electric immersion heater for heating the contents and an outlet equipped with a stopper at the bottom portion thereof. Since vacuum distillation is required in some cases, a reaction bath which is capable of vacuum distillation is preferred.

When the capsaicine compound is produced, if a solvent having a specific gravity larger than that of water is used and washing with water is carried out in the after-treatment, the capsaicine compound comes to a lower layer. For this reason, it is preferable to connect a storage vessel for the capsaicine compound with the outlet. In this case, after the water layer is discharged from the outlet, the capsaicine compound is returned to the reaction vessels for microencapsulation. These series of operations are usually carried out in a closed system.

In the microencapsulating step, the conditions for microencapsulation must be adequately determined so as to efficiently microencapsule the most of the capsaicine compound. Not only one-stage microencapsulation but also multi-stage microencapsulation may be adopted in some cases. The mean particle diameter of the microcapsules may be so selected as to be optimum for their use by considering the microencapsulating conditions mentioned above.

The outline of the method for producing the microcapsules is mentioned previously, but illustrated in detail as follows. The present invention adopts a microencapsulating method comprising the steps of dispersing a water-insoluble or -slightly soluble capsaicine compound in water and forming polymer walls, which are insoluble in core materials containing the capsaicine compound and water, on the surfaces of the dispersed particles by an oil-in-water type polymerization method such as an interfacial polymerization method and an In-situ polymerization method which will be described in the following. The oil-in-water type polymerization method adopted in the present invention is not restricted to these two methods.

The interfacial polymerization method will first be explained.

An oil-soluble raw wall material A is dissolved in the hydrophobic core materials containing the capsaicine compound, and water and an auxiliary material such as a dispersant are added to the solution. The resultant mixture is stirred at predetermined stirring conditions so as to form a system in which the solution of the hydrophobic core material and the oil-soluble raw wall material A are dispersed in the water phase at a predetermined particle diameter. Under stirring this system, an aqueous solution of a water-soluble raw wall material B is added thereto so as to react both the raw wall materials on the interfaces between the dispersed particles and water phase to form polymer capsule walls which are insoluble to both the core materials and the water phase and to produce microcapsules containing the hydrophobic core materials (one-stage microencapsulating method).

A multi-stage microencapsulating method may be adopted in order to minimize the amount of the capsaicine compound remaining not microencapsulated. A solvent which is slightly soluble in water, which has a high solubility to the capsaicine compound and in which an oil-soluble raw wall material C is dissolved, is added to the microencapsulated system as it is or after the solvent is dispersed in water, and a water-soluble raw wall material D is reacted under predetermined stirring conditions and temperature conditions so as to form polymer walls again (two-stage-microencapsulating method). This operation is repeated several times to efficiently microencapsulate the capsaicine compound remaining not microencapsulated to minimize the amount of the capsaicine compound remaining not microencapsulated (multi-stage microencapsulating method).

The oil-soluble raw wall materials A and C and the water-soluble raw wall materials B and D, respectively, may be either different or the same. Examples thereof are as follows.

As examples of the oil-soluble wall material there may be mentioned poly-isocyanates, polybasic carboxylic acid chlorides and polybasic sulfonic acid chloride. For example, they are hexamethylene diisocyanate, trimethylhexamethylene diisocyanate, isophorone diisocyanate, phenylene diisocyanate, toluene diisocyanate, xylylene diisocyanate, naphthalene diisocyanate, polymethylene polyphenyl diisocyanate, sebacoyl dichloride, adipoyl dichloride, azeloyl dichloride, terephthaloyl dichloride, trimesoyl dichloride and benzenesulfonyl dichloride.

As examples of the water-soluble raw wall material there may be mentioned polyfunctional amines and polyhydric compounds. For example, they are ethylene diamine, hexamethylene diamine, phenylene diamine, diethylene triamine, triethylene tetramine, piperazine, ethylene glycol, butanediol, hexanediol and polyethylene glycol.

An In-situ polymerizing method will be explained.

An In-situ polymerization method is a method of producing microcapsules by dissolving raw wall materials either in the hydrophobic core materials containing the capsaicine compound or a water phase and dispersing the hydrophobic core materials in the water phase so as to form polymer walls which are insoluble to both the hydrophobic core materials and the water phase on the interfaces between the dispersed particles and the water phase. This method is different from an interface polymerization method. In the present invention, after producing a dispersion in water of the microcapsules of the synthesized capsaicine compound (one-stage microencapsulating method), polymer walls which are insoluble to both the hydrophobic core materials and the water may be further formed on the interfaces between the dispersed particles and the water phase (1) by dispersing the hydrophobic core material which is a solvent having a high solubility of the capsaicine compound, being slightly soluble in water and dissolving an oil-soluble raw wall material E therein in this system or (2) by adding a water-soluble raw wall material F to this system as it is or in the form of an aqueous solution after dispersing a solvent having a high solubility of the capsaicine compound and being slightly soluble in water in this system (two-stage microencapsulating method). By repeating this operation several times, the capsaicine compound remaining not microencapsulated is effectively microencapsulated, thereby minimizing the amount of the capsaicine compound remaining not microencapsulated (multi-stage microencapsulating method).

Examples of the raw wall materials E and F are as follows. As the oil-soluble raw wall material E, a material which forms polymer by the radical polymerization such as acrylate, methacrylate, vinyl acetate, styrene, divinylbenzene, ethylene dimethacrylate and the like is used. As the water-soluble raw wall material F, a material which forms polymer by condensation polymerization such as urea/formalin, melamine/formalin, phenol/formalin and the like is preferable.

The type and the amount of the raw wall material used in the present invention is selected in accordance with the kind of the core material and the purpose for which microcapsules are used. In the present invention, a multi-stage microencapsulating method in which the interface polymerization method and the In-situ polymerization method are combined may be adopted.

As the auxiliary agent used for microencapsulation, a dispersant for dispersing the hydrophobic core materials in the water phase is mentioned. More specifically, natural polysaccharides such as acacia gum, sodium alginate, locust bean gum and xanthane gum, semi-synthesized polysaccharides such as carboxymethyl cellulose and methyl cellulose and synthesized polymers such as polyvinyl alcohol are used either singly or in the form of a mixture. The amount of dispersant used is ordinarily 0.01 to 10.0%, preferably 0.1 to 3.0% based on the suspension composition at the point of time in which microencapsulation is carried out. If necessary, at least one surfactant such as polyoxyethylene alkyl ether, polyoxyethylene alkylaryl ether, alkylphenyl condensate ether, polyoxyethylene alkyl ester, polyoxyethylene alkylamino ether, polyoxyethylene alkylamide, polyoxyethylene polyoxypropylene block polymer, polyoxyethylene vegetable oil ether, sorbitan fatty acid ester and polyoxyethylene sorbitan fatty acid ester is used. The amount of the surfactant used is ordinarily not more than 10%, preferably not more than 3% based on the dispersion. In the case of producing the core material for microcapsules by dissolving the capsaicine compound in a solvent, at least one solvent selected from ethers such as butyl ether and ethylvinyl ether, aliphatic or aromatic hydrocarbons such as heptane and xylene, halogenated hydrocarbons such as dichloromethane and trichloroethane, mineral oils such as machine oil, vegetable oils and solvents which are mainly used as a plasticizer for resins such as phthalate, adipate, phosphate, maleate and low-molecular epoxy compounds is used. As other adjuvants, an anti-mold agent and a specific gravity adjuster, and further a stabilizer and a pH adjuster for some capsaicine compound may be added to the core material and/or the water phase.

As a result of the production of the capsaicine compound by the above method, a capsaicine compound having a strong irritant nature even in a slight amount thereof can be synthesized from a starting material having practically no irritant nature, and the microcapsules of the capsaicine compound can be produced in the same bath with a very small amount of the capsaicine compound remaining not microencapsulated. Thus, an agent having a slight irritant nature and easy to handle can be obtained without the need for the direct touch thereof by the workers in the production.

In the resin molding composition and its molded article (product) of this invention, the resin in which the microcapsules filled with the capsaicine compound as a core material is to be contained is not restricted to the particular types. It is possible to use various types of resins such as semisynthetic resins, genuine synthetic resins, natural resins, synthetic rubbers, copolymer resins and plastic alloys obtained by mixing or grafting two or more types of resin. These types of resin may be used either singly or in combination.

As examples of the semisynthetic resins in the composition of this invention there may be mentioned nitrocellulose, acetylcellulose, cellulose propionate, methyl cellulose, ethyl cellulose, carboxymethyl cellulose and the like. Examples of the genuine synthetic thermoplastic resins are polyethylene, polystyrene, polypropylene, methacryl resin, vinyl chloride resin, polyamide resin, fluorine resin, silicone resin, polycarbonate, polyether resin and the like. As examples of the thermosetting resins usable in this invention there may be mentioned phenol resin, furfural resin, xylene resin, urea resin, melamine resin, guanamine resin, unsaturated-polyester resin, diallyl phthalate resin, alkyd resin, furan resin, aniline resin, epoxy resin, polyurethane resin, polyimide resin and the like. The synthetic rubbers usable in the composition of this invention include diene type, olefin type, acryl type, silicone type, fluorine type and other types of rubber. Examples of the natural resins are copal resin, rosin, natural rubber and vulcanized natural rubber. The types of resin most favorably used for the purpose of this invention are genuine synthetic thermoplastic resins or thermoplastic rubbers which are easy to work. These resins are most suited for use with the capsaicine compounds which are not influenced by heat. The resin may be added with a suitable adjuvants such as plasticizer, stabilizer, flame retardant, lubricant, coloring matter, filler, antioxidant, ultraviolet absorber, etc., for improving molding workability and stability of the composition. Also, the composition may be subjected to a treatment (s) with a pest control agent, a plant regulating agent and/or the like so that the composition will have additional effect (s) in use.

The typical modes of use of the resin molded articles (products) of this invention are as follows:

1) Incorporation into the articles mainly made of a thermoplastic resin, cables for electrical and optical communication, power transmission, etc., cords for electrical apparatus and wiring, etc.

2) Treatment on furnishings, interior and exterior materials for buildings, containers, hoses, pipes, plates, packages, packaging materials, etc.

3) Treatment on yarns or threads in textile goods.

Treatment on various types of tapes and sheets, and application (by attachment, winding, etc.) to the objects (machine parts, equipment, trees, etc.) which are to be protected from gnawing damage by the animals.

5) Kneading with sealants and various resin-based pasty products for closing the entrances of rodents and other animals into buildings etc.

The resin molding composition and its molded articles containing capsaicine compounds for preventing gnawing damage by the animals according to the present invention have an excellent effect of preventing gnawing damage by the animals. Especially, in the case of the capsaicine compounds microencapsuled with a melamine resin film have a high effect. The effect is particularly high with the microcapsules of which 90% or more have a particle diameter in the range of 5 to 100 μm, with the mean particle diameter being 15 to 50 μm.

Also, the composition of this invention has good molding workability owing to its excellent water and heat resistance, is very small in reduction of efficacy in the course of molding process, and can maintain the constant efficacy for a long time. Further, the articles (products) molded from the composition with a resin are notably lessened in pungency and stimulus to man and therefore easy to handle. And the process for synthesizing a capsaicine compound and producing microcapsules thereof, in succession, in one-bath of the present invention is industrially very advantageous.

EXAMPLES

The present invention will be further described below with reference to the examples thereof. (In the following descriptions, all "parts" are by weight unless other wise noted.)

Example 1

10 parts of nonylic acid vanillylamide and 10 parts of a Millionate MR-400 (produced by Nippon Urethane Co., Ltd.) were dissolved in 75 parts of dioctyl phthalate, and this solution was dispersed in 300 g of a 1% aqueous solution of polyvinyl alcohol [Gosenol GH-17 (produced by The Nippon Synthetic Chemical Industry Co., Ltd.)] with stirring at 650 rpm for 10 min. using above-mentioned mixer to prepare an O/W emulsion. In the meantime, 2.5 g of ethylenediamine and 2.5 g of diethylenetriamine were dissolved in 95 g of water, and this solution was added dropwise to said emulsion with stirring at 250 rpm allowing them to react at 60° C. for 3 hours to prepare the suspended-in-water microcapsules (mean particle diameter: 49 µm) with a polyurea wall. The suspension was dried by a spray dryer to obtain the microcapsules each containing 10% of nonylic acid vanillylamide. 2parts of these microcapsules were added to 98 parts of Vinyl compound SE-24 (produced by Mitsui Toatsu Chemical Inc.), and the mixture was subjected to the same rolling treatment as conducted in Control Example 1 mentioned below to obtain a 1 mm thick polyvinyl chloride sheet containing 0.2% of nonylic acid vanillylamide.

Example 2

10 parts of nonylic acid vanillylamide and 20 parts of sebacoyl chloride were dissolved in 65 parts of dioctyl phthalate, and this solution was dispersed in 200 parts of a 1% aqueous solution of Gasenol GH-17 with stirring at 1200 rpm for 10 min. using above-mentioned mixer to prepare an O/W emulsion. In the meantime, 5 parts of ethylenediamine, 5 parts of diethylenetriamine and 10 parts of sodium hydroxide were dissolved in 80 parts of water, and this solution was added dropwise to said emulsion with stirring at 250 rpm, causing a reaction to take place, the reaction being allowed to continue at 60° C. for 3 hours to prepare the suspended-in-water microcapsules having a polyamide wall.

95% of the produced microcapsules had a particle diameter in the range of 5 to 100 µm, the mean particle diameter being 23 µm. The suspended microcapsules were dried by a spray dryer to obtain the microcapsules each containing 10% of nonylic acid vanillylamide. 2 parts of these microcapsules were added to 98 parts of Vinyl compound SE-24, and the mixture was subjected to the same rolling treatment as conducted in Control Example 1 to obtain a 1 mm thick polyvinyl chloride sheet containing 0.2% of nonylic acid vanillylamide.

Example 3

10 parts of nonylic acid vanillylamide was dissolved in 70 parts of dioctyl adipate, and this solution was added to 200 parts of a 3% aqueous solution of pH 4.5 prepared by dissolving a styrene-maleic anhydride resin and a small quantity of sodium hydroxide in water and stirred with a mixer (1 liter) at 25° C. 1200 rpm for 5 minutes to form an O/W emulsion. Then 35 parts of a 50% aqueous solution of Sumilez Resin 613 (a melamine-formaldehyde prepolymer produced by Sumitomo Chemical Co., Ltd.) was added dropwise to said emulsion with stirring at 250 rpm and stirring was continued at 70° C. for 3 hours to prepare the suspended-in-water microcapsules having a melamine resin capsule wall. 92% of the produced microcapsules had a diameter in the range of 5 to 100 µm, the mean particle diameter being 28 µm.

The produced microcapsules were dried and added with Vinyl compound SE-24 and the mixture was subjected to a rolling treatment, all in accordance with Control Example 1, to make a 1 mm thick polyvinyl chloride sheet containing 0.2% of nonylic acid vanillylamide.

Example 4

10 parts of nonylic acid vanillylamide was dissolved in 65 parts of dioctyl phthalate, and this solution was dispersed in 200 parts of a 3% aqueous solution (pH 4.5) of styrene-maleic anhydride resin and a small quantity of sodium hydroxide and the whole was charged into round-bottomed flask (1 liter) with 7 cm-length stirring brade and stirred at 85° C., 700 rpm for 30 minutes to prepare an O/W emulsion. Then 50 parts of a 50% aqueous solution of a melamine-formaldehyde prepolymer Sumilez Resin 613 (produced by Sumitomo Chemical Co., Ltd.) was added dropwise to said emulsion-with stirring at 350 rpm. Stirring was carried on at 70° C. for 3 hours to form the suspended-in-water microcapsules having a melamine resin capsule wall. 94% of these microcapsules had a particle diameter in the range of 5 to 100 µm, the mean particle diameter being 25 µm.

The thus produced microcapsules were dried, added with Vinyl compound SE-24 and subjected to a rolling treatment in the same way as in Control Example 1 to make a 1 mm thick polyvinyl chloride sheet containing 0.2% of nonylic acid vanillylamide.

Example 5

Suspended-in-water microcapsules having a melamine resin wall were produced by following the same procedure as Example 4 except for change of the dispersing conditions (dispersing at 1000 rpm). 86% of these microcapsules had a particle diameter of 5 to 100 µm, the mean particle diameter being 10 µm. The produced microcapsules were dried, added with Vinyl compound SE-24 and subjected to a rolling treatment according to the formula of Control Example 1 to form a 1 mm thick polyvinyl chloride sheet containing 0.2% of nonylic acid vanillylamide.

Example 6

Suspended-in-water microcapsules having a melamine resin wall were prepared according the same procedure as Example 4 except for change of the dispersing conditions (dispersing at 500 rpm). 72% of the produced microcapsules had a particle diameter in the range of 5 to 100 µm, the mean particle diameter being 65 µm. The thus obtained microcapsules were dried and added with Vinyl compound SE-24 and the mixture was subjected to a rolling treatment according to the process of Control Example 1 to make a 1 mm thick polyvinyl chloride sheet containing 0.2% of nonylic acid vanillylamide.

Example 7

58.5 parts of 4-hydroxy-3-methoxybenzylamine hydrochloride, 200 parts of benzene and 200 parts of water were charged into a reaction vessel equipped with a three-one motor the rotational frequency of which is variable and an outlet having a stopper at the bottom portion and stirred. 58 parts of potassium carbonate was added to the mixture and further 54 parts of pelargonoyl chloride was added dropwise to the resultant mixture at room temperature. In this state, the mixture was stirred for 3 hours until the end of the reaction. After the stirring was stopped and the mixture was allowed to stand for 30 minutes, the water layer in the lower layer was discharged from the bottom portion. The residue was distilled under a reduced pressure to remove the solvent almost completely, thereby obtaining crude nonylic acid vanillylamide. As a result of quantitative analysis of a slight amount of product by high pressure liquid chromatography (hereinunder referred to as "HPLC"), the purity of nonylic acid vanillylamide was determined to be 91.7%. The irritant nature thereof to skin, especially, to mucosae was strong.

Thereafter, 148 parts of dioctyl phthalate was charged into the reaction vessel and stirred. 400 parts of 3% aqueous solution Of pH 4.5 prepared by dissolving a styrene-maleic anhydride resin and a small quantity of sodium hydroxide in water were charged into the vessel and stirred with a mixer at 25° C., 750 rpm for 20 minutes to form an O/W emulsion.

Then 400 parts of a 50% aqueous solution of Sumilez Resin 613 was added dropwise to said emulsion with stirring at 230 rpm and stirring was continued at 70° C. for 3 hours to prepare the suspended-in-water microcapsules having a melamine resin capsule wall. 92% of the produced microcapsules had a diameter in the range of 5 to 100 μm, the mean particle diameter being 37 μm. The suspension was dried by a spray dryer to obtain the microcapsules containing 20% of nonylic acid vanillylamide. 1 part of these microcapsules were added to 99 parts of Vinyl compound SE-24, and the mixture was subjected to the same rolling treatment as conducted in Control Example 1 mentioned below to obtain a 1 mm thick polyvinyl chloride sheet containing 0.2% of nonylic acid vanillylamide.

Example 8

Nonylic acid vanillylamide was synthesized in the same way as in Example 7. The purity was determined to 93.3%. The irritant nature thereof to skin, especially, to mucosae was strong.

Thereafter, 502 parts of diisodecyl adipate was charged into the reaction vessel and stirred. 600 parts of 3% aqueous solution of pH 4.5 prepared by dissolving a styrene-maleic anhydride resin and a small quantity of sodium hydroxide in water were charged into the vessel and stirred with a mixer at 25° C., 750 rpm for 30 minutes to form an O/W emulsion.

Then 500 parts of a 50% aqueous solution of Sumilez Resin 613 (a melamine-formaldehyde prepolymer produced by Sumitomo Chemical Co., Ltd.) was added dropwise to said emulsion with stirring at 250 rpm and stirring was continued at 70° C. for 3 hours to prepare the suspended-in-water microcapsules having a melamine resin capsule wall. 95% of the produced microcapsules had a diameter in the range of 5 to 100 μm, the mean particle diameter being 31 μm. The suspension was dried by a spray dryer to obtain the microcapsules containing 10% of nonylic acid vanillylamide. 2 parts of these microcapsules were added to 98 parts of Vinyl compound SE-24, and the mixture was subjected to the same rolling treatment as conducted in Control Example 1 mentioned below to obtain a 1 mm thick polyvinyl chloride sheet containing 0.2% of nonylic acid vanillylamide.

Example 9

58.5 parts of 4-hydroxy-3-methoxybenzylamine hydrochloride, 200 parts of benzene and 200 parts of water were charged into a reaction vessel equipped with a three-one motor the rotational frequency of which is variable and an outlet having a stopper at the bottom portion and stirred. 58 parts of potassium carbonate was added to the mixture and further 54 parts of pelargonoyl chloride was added dropwise to a resultant mixture at room temperature. In this state, the mixture was stirred for 3 hours until the end of the reaction. After the stirring was stopped and the mixture was allowed to stand for 30 minutes, the water layer in the lower layer was discharged from the bottom portion. The residue was distilled under a reduced pressure to remove solvent almost completely, thereby obtaining crude nonylic acid vanillylamide. As a result of quantitative analysis of a slight amount of product by HPLC, the purity of nonylic acid vanillylamide was determined to be 92.1%. The irritant nature thereof to skin, especially, to mucose was strong.

Thereafter, 85.6 parts of dioctyl phthalate, 25.7 parts of Millionate 3040 and 5.1 parts of New Kalgen D-230 (produced by Takemoto Fat and Oil Co., Ltd.) were charged into the reaction vessel and stirred. 284 parts of a 1% aqueous solution of acacia gum was further added to the mixture and stirred. By stirring the resultant mixture at a rate of 650 rpm for 10 minutes, a dispersion system was obtained. The rotational frequency of the motor was then lowered to 250 rpm and 42.8 parts of an aqueous solution with 4.3 parts of ethylene diamine and 4.3 parts of diethylene triamine dissolved therein was gradually added dropwise to the system. Thereafter, the liquid temperature was raised to 60° C. to bring about a reaction for 2 hours, thereby producing microcapsules of a suspension in a first stage (the rate at which nonylic acid vanillylamide was-remained not encapsulated outside of the microcapsules (hereinunder referred to as "liberation rate") was 1.5%).

Since the irritant nature of this agent is considerably reduce, it is usable for some purposes as it is, but in order to further reduce the irritant nature, microencapsulation in a second stage was carried out. A liquid mixture of 85.6 parts of dioctyl phthalate, 17.1 parts of Millionate 3040 and 3.4 parts of New Kalgen D-230 was prepared in another reaction vessel of the same type. 171 parts of a 1% aqueous solution of acacia gum was added to the mixture and the mixture was stirred at a rate of 650 rpm for 10 minutes to obtain a dispersion. The dispersion was added to the microcapsules of a suspension in the first stage and the resultant mixture was stirred at 250 rpm for 15 minutes. 42.8 parts of an aqueous solution with 4.3 parts of ethylene diamine and 4.3 parts of diethylene triamine dissolved therein was gradually added dropwise to the suspension. Thereafter, the liquid temperature was raised to 60° C. to bring about a reaction for microencapsulation in a second stage, thereby producing 850 parts of microcapsules of a suspension containing 9% of nonylic acid vanillylamide in a second stage. The liberation rate was 0.2% and the irritant nature was very weak. Dioctyl phthalate used in the microencapsulation was a solvent, Millionate 3040 was an oil-soluble raw wall material, ethylene diamine and diethylene triamine were water-soluble raw wall materials and New Kalgen D-230 and acacia gum were dispersants.

The liberation ratio was expressed by a percentage obtained in the following method. 500 mg of a sample was added to 500 ml of distilled water and the mixture was shaken for 30 minutes. The mixture liquid was then filtered through a membrane filter (0.2 μm) and nonylic acid vanillylamide was quantitatively analyzed by an HPLC. The value obtained was divided by the quantitative value before microencapsulation to obtain the liberation rate (rate of capsaicine compound remained not encapsulated). The liberation rate was measured in the same way in the following examples.

2.25 parts of these microcapsules were added to 97.75 parts of Vinyl compound SE-24, and the mixture was subjected to the same rolling treatment as conducted in Control Example 1 mentioned below to obtain a 1 mm thick polyvinyl chloride sheet containing 0.2% of nonylic acid vanillylamide.

Example 10

By using a similar reaction vessel to that in Example 9, 5.7 parts of 8-methylnon-trans-6-enoyl chloride and 0.2 part of pyridine were added to a solution of 4.7 parts of 4-hydroxy-3-methoxybenzylamine in 25 parts of diethyl ether, and the mixture was stirred at room temperature for 4 hours. After 10 parts of water was added to the mixture and stirred for 5 minutes, the resultant mixture was allowed to stand for 5 minutes. The water layer in the lower layer was discharged. By almost completely removing ether under a reduced pressure, crude (E)-N-(4-hydroxy-3-methoxybenzyl)-8-methylnon- 6-enamide was obtained. As a result of quantitative analysis of a slight amount of product by an HPLC, the purity of (E) -N-(4-hydroxy-3-methoxybenzyl)-8-methylnon- 6-enamide was determined to be 90.5%. The irritant nature thereof to skin, especially, to mucosae was strong as nonylic acid vanillylamide obtained in Example 9.

Thereafter, 21.5 parts of dimethyl phthalate, 3.0 parts of sebacoyl dichloride, 3.0 parts of Millionate FIR-400 and 0.1 part of Emalgen 910 (produced by Kao Corporation) were charged into the reaction vessel and stirred to obtain a uniform mixture liquid. 50.0 parts of a 1.5% aqueous solution of Gosenol GH-17 (produced by The Nippon Synthetic Chemical Industry Co., Ltd. ) -was added to the mixture liquid and the resultant mixture was stirred at a rate of 650 rpm for 10 minutes, thereby obtaining a dispersion system. The rotational frequency of the motor was then lowered to 250 rpm and 13.9 parts of an aqueous solution with 1.0 part of sodium hydroxide, 1.0 part of ethylene diamine and 1.0 part of diethylene triamine dissolved therein was gradually added dropwise to the system. Thereafter, the liquid temperature was raised to 60° C. to bring about a reaction for 2 hours, thereby producing microcapsules of a suspension containing 7.5% of N-(4-hydroxy-3-methoxybenzyl) -8-methylnon- 6-enamide. The liberation rate thereof was as low as 0.6%. The irritant nature was greatly reduced and the agent was easy to handle.

Dimethyl phthalate used for the microencapsulation is a solvent, sebacoyl dichloride and Millionate MR-400 are oil-soluble film materials, sodium hydroxide, ethylene diamine and diethylene triamine are water-soluble film materials and Emalgen 910 and Gosenol GH-17 are dispersants.

2.67 parts of these microcapsules were added to 97.33 parts of Vinyl compound SE-24, and the mixture was subjected to the same rolling treatment as conducted in Control Example 1 mentioned below to obtain a 1 mm thick polyvinyl chloride sheet containing 0.2% of nonylic acid vanillylamide.

Example 11

Nonylic acid vanillylamide was synthesized in the same way as in Example 9 except for using 171.2 parts of dioctyl adipate in place of 200 parts of benzene. After the stirring was stopped and the mixture was allowed to stand for 30 minutes, the water layer in the lower layer was discharged from the bottom portion. As a result of quantitative analysis of a slight amount of dioctyl adipate solution in the reaction vessel by an HPLC, the purity of nonylic acid vanillylamide was determined to be 30.3%. The irritant nature thereof to skin, especially, to mucosae was strong as the product obtained in Example 9.

Thereafter, 42.8 parts of Millionate MR-200 and 8.8 parts of New Kalgen D-410 were charged into the reaction vessel and stirred. 455 parts of a 2% aqueous solution of acacia gum was further added to the mixture and stirred at a rate of 650 rpm for 10 minutes to obtain a dispersion system. The rotational frequency of the motor was then lowered to 250 rpm and 85.6 parts of an aqueous solution with 8.6 parts of ethylene diamine and 8.6 parts of diethylene triamine dissolved therein was gradually added dropwise to the system. Thereafter, the liquid temperature was raised to 60° C. to bring about a reaction for microencapsulation for 2 hours, thereby producing 850 parts of microcapsules of a suspension containing 9% of nonylic acid vanillylamide. The liberation rate thereof was 0.9%. The irritant nature was greatly reduced.

2.25 parts of these microcapsules were added to 97.75 parts of Vinyl compound SE-24, and the mixture was subjected to the same rolling treatment as conducted in Control Example 1 mentioned below to obtain a 1 mm thick polyvinyl chloride sheet containing 0.2% of nonylic acid vanillylamide.

Example 12

Nonylic acid vanillylamide was synthesized in the same way as in Example 9 except for using 71.2 parts of cyclohexane and 100 parts of dioctyl phthalate in place of 200 parts of benzene. After the stirring was stopped and the mixture was allowed to stand for 30 minutes, the water layer in the lower layer was discharged from the bottom portion. As a result of quantitative analysis of a slight amount of solution in the vessel by an HPLC, the purity of nonylic acid vanillylamide was determined to be 30.6%. The irritant nature thereof to skin, especially, to mucosae was strong as the product obtained in Example 9.

Thereafter, 22.8 parts of Millionate MR-200 and 8.5 parts of New Kalgen D-225 (produced by Takemoto Fat and Oil, Co., Ltd.) were charged into the reaction vessel and stirred. 455 parts of a 1.5% aqueous solution of Gosenol GH-17 was further added to the mixture and stirred at a rate of 650 rpm for 10 minutes to obtain a dispersion system. The rotational frequency of the motor was then lowered to 250 rpm and 85.6 parts of an aqueous solution with 8.6 parts of ethylene diamine and 8.6 parts of diethylene triamine dissolved therein was gradually added dropwise to the system. Thereafter, the liquid temperature was raised to 60° C. to bring about a reaction for microencapsulation for 2 hours, thereby producing 850 parts of microcapsules of a suspension containing 9% of nonylic acid vanillylamide. The liberation rate thereof was 0.9%. The irritant nature was greatly reduced.

The microcapsules were dried by a spray drier to almost completely remove the water content and cyclohexane. Thus, 250 parts of microcapsules of a powder containing about 30% of nonylic acid vanillylamide was produced. The liberation rate thereof was 1.0%. The irritant nature was weak.

0.67 parts of these microcapsules were added to 99.33 parts of Vinyl compound SE-24, and the mixture was subjected to the same rolling treatment as conducted in Control Example 1 mentioned below to obtain a 1 mm thick polyvinyl chloride sheet containing 0.2% of nonylic acid vanillylamide.

Control Example 1

0.2 part of capsaicine compound was added to 99.8 parts of a commercial vinyl compound containing a plasticizer, a pigment, etc. (Vinyl compound SE-24), and the mixture was subjected to hot rolling by a heated pressure roll (Model NS-105(J) W mfd. by Nishimura Machinery Co., Ltd.) at 180° C. for 10 minutes to obtain a 1 mm thick polyvinyl chloride sheet containing 0.2% of capsaicine compound.

Control Example 2

0.6 part of a methanol extract of capsicum containing 35% of capsaicine compound was added to 99.4 parts of Vinyl compound SE-24, and the mixture was subjected to the same rolling treatment as conducted Control Example 1 to obtain a 1 mm thick polyvinyl chloride sheet containing 0.2% of capsaicine compound.

Control Example 3

0.2 part of nonylic acid vanillylamide was added to 99.8 parts of Vinyl compound SE-24, and the mixture was subjected to the same rolling treatment as performed in Control Example 1 to obtain a 1 mm thick polyvinyl chloride sheet containing 0.2% of nonylic acid vanillylamide.

Control Example 4

Vinyl compound SE-24 alone was subjected to the same hot rolling treatment as conducted in Control Example 1 to form a 1 mm thick polyvinyl chloride sheet.

Test Example 1-1

Effect for preventing gnawing damage, by rodents Test method

Each of the sheets obtained in Control Example 1, Control Example 2, Control Example 3, Control Example 4 and Example 1 was cut to a size of 75×150 mm. It was then folded double and, after placing therein 2 cakes of solid feed for rodents, stapled at three edge points to prepare a test specimen. Each of the thus prepared specimens was placed in a cage in which three rodents with a body weight of about 300 g had been put, and after leaving this situation overnight, the area of the sheet which sustained gnawing damage by the rodents was examined. One specimen using the sheet obtained in one of Control Examples 1–4 and Example 1 was placed in each cage, and the test was conducted on 5 cages for each specimen.
Results

| Specimen | Area of gnawing damage (cm$^2$) | | | | | |
|---|---|---|---|---|---|---|
| | Cage No. | | | | | |
| | 1 | 2 | 3 | 4 | 5 | Average |
| Control Example 1 | 0 | 0.2 | 0.4 | 0 | 0 | 0.12 |
| Control Example 2 | 0 | 0.1 | 0 | 0.4 | 0 | 0.10 |
| Control Example 3 | 0.1 | 0 | 0.3 | 0 | 0.3 | 0.14 |
| Control Example 4 | 14.5 | 8.9 | 22.0 | 9.5 | 18.2 | 14.6 |
| Example 1 | 0 | 0 | 0 | 0 | 0 | 0 |

The specimen of Example 1 showed a prominent effect of preventing gnawing damage and high practical applicability in comparison with the specimen of the Control Examples. It is remarkable that the sheet containing the microcapsules prepared in Example 1 sustained no gnawing damage at all. In the case of the Control Examples, the feed in the specimen in each cage has been eaten.

Test Examples 1-2

Effect for preventing gnawing damage by rodents
Test method

The test specimens, prepared in the same way as in Test Example 1-1 but by using the sheets obtained in Examples 2 to 12 and Control Example 4, were placed in the respective cages (one specimen in each cage having 3 rodents penned therein), and after leaving the things as they were for a whole day, the area of each sheet which sustained gnawing damage by the rodents was examined.
Results

| Specimen | Area of gnawing damage (cm$^2$) | | | | | |
|---|---|---|---|---|---|---|
| | Cage No. | | | | | |
| | 1 | 2 | 3 | 4 | 5 | Average |
| Example 2 | 0.7 | 3.3 | 0 | 1.0 | 2.5 | 1.50 |
| Example 3 | 0 | 0.1 | 0 | 0 | 0.2 | 0.06 |
| Example 4 | 0 | 0 | 0 | 0.1 | 0 | 0.02 |
| Example 5 | 0 | 0.2 | 0.1 | 1.2 | 0.6 | 0.42 |
| Example 6 | 0.1 | 1.3 | 0 | 0.9 | 0.2 | 0.50 |
| Example 7 | 0.1 | 0.1 | 0 | 0 | 0 | 0.04 |
| Example 8 | 0 | 0 | 0.2 | 0 | 0 | 0.04 |
| Example 9 | 0 | 0.7 | 2.3 | 1.5 | 2.0 | 1.3 |
| Example 10 | 2.1 | 0.8 | 2.3 | 1.7 | 1.3 | 1.3 |
| Example 11 | 2.0 | 1.2 | 2.2 | 1.0 | 0.6 | 1.4 |
| Example 12 | 2.0 | 1.2 | 2.2 | 1.0 | 0.6 | 1.4 |
| Control Example 4 | 11.3 | 18.7 | 9.8 | 21.5 | 15.2 | 15.3 |

The specimen of each of Example 2 to 12 showed a prominent effect of preventing gnawing damage and high practical applicability in comparison with the specimen of the Control Example 4. It is notable that the microcapsules having a melamine wall prepared in Examples 3, 4, 5, 6, 7 and 8 showed higher gnawing damage preventive effect than the microcapsules having a polyamide wall prepared in Example 2. Further, the microcapsules of which 90% or more had a particle diameter in the range of 5 to 100 μm and an mean particle diameter of 15 to 50 μm, prepared in Examples 3, 4, 7 and 8 showed better gnawing damage preventive effect than the microcapsules of which particle size and mean particle diameter were not confined within said ranges, which were prepared in Examples 5 and 6.

Test Example 2-1

Test on pungency and dermal stimulus to man
Test method (Pungency)

An organoleptic test for pungency was conducted by letting the subjects lick the sheets obtained in the respective Examples or Control Examples and the component substances, that is, capsaicine compound, nonylic acid vanillylamide and methanol extract of capsicum used for making the sheets.

(Derreal stimulus)

A 3 cm$^2$ piece of each sheet was attached to an inside region of an arm of each subject while each component substance was applied in a small amount (about 1 mg) to a similar region, and the stimulus felt by each subject during the period of 2 hours after application was examined.
Results (Pungency)

Each subject felt severe pungency in the whole mouth when only a very small amount of each component substance was put on the tip of the tongue, but every subject felt only a slight degree of pungency when he licked the sheet containing the microcapsules prepared in Example 1. Although the sheets of Control Examples 1, 2 and 3 gave a sense of relatively strong pungency, they had enough practicability.

(Dermal stimulus)

Each component substance gave a tingling stimulus on application, but not such stimulus was felt with the sheets obtained in Example 1.

Test Example 2-2

Test on pungency and dermal stimulus to man
Test method

The same test as practiced in Test Example 2-1 was conducted on the sheets of Examples 2~12.
Results
(Pungency)

The sheets containing the microcapsules obtained in Examples 2~12, when licked, gave only a slight sense of pungency.

(Dermal stimulus)

The sheets containing the microcapsules obtained in Examples 2~12 gave no sense of dermal stimulus.

Test Example 3-1

Determination of free components on sheet surface
Test method

Two sheets (5×5 cm) of Control Examples 1, 2 and Examples 1, 7, 8 respectively, were washed under shaking with 50 ml of distilled water for 3 hours, and the capsaicine compound in the washings were quantified by liquid chromatography. The percentage of the quantified amount of the capsaicine compound to the amount of the capsaicine compound contained in the specimen was calculated and given as free component ratio.
Results

|  | Control Example 1 | Control Example 2 | Example 1 | Example 7 | Example 8 |
|---|---|---|---|---|---|
| Free component ratio (%) | 0.48 | 0.42 | 0.16 | 0.14 | 0.17 |

The free component ratio of the sheet containing the microcapsules obtained in Examples 1, 7, 8 were less than half that of Control Examples 1 and 2.

Test Example 3-2

Determination of free components on sheet surface
Test method

Specimens were prepared with the sheets of Examples 2–6 and 7, 11 and the free component ratio was determined in the same way as in Test Example 3-1.

Results

|  | Ex. 2 | Ex. 3 | Ex. 4 | Ex. 5 | Ex. 6 | Ex. 7 | Ex. 11 |
|---|---|---|---|---|---|---|---|
| Free component ratio (%) | 0.25 | 0.11 | 0.09 | 0.10 | 0.18 | 0.10 | 0.12 |

The free component ratio was very low in each specimen, indicating no problem as in the case of Test Example 3-1.

What is claimed is:

1. Microcapsules containing capsaicine compound as an effective component for use in preventing gnawing damage by animals in which the mean particle diameter of the microcapsules is 15 to 50 μm and 90% or more of the microcapsules have a particle diameter in the range of 5 to 100 μm, said microcapsules having a melamine resin wall material.

2. The microcapsules according to claim 1, wherein the capsaicine compound is nonylic acid vanillylamide or capsaicine.

3. A continuous process for producing a capsaicine compound and microcapsules thereof in one bath comprising me steps of:

preparing a capsaicine compound represented by the following general formula (1):

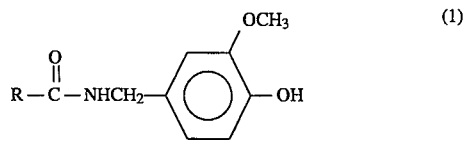

wherein R represents an alkyl or alkenyl group, each of the groups having 7 to 12 carbon atoms, by condensing a compound represented by the following general formula (2):

wherein R represents an alkyl or alkenyl group, each of the groups having 7 to 12 carbon atoms and Hal represents a halogen atom, and vanillyamine or a salt thereof in a reaction bath in a solvent;

dispersing the capsaicine compound in water in the same reaction bath without separating the capsaicine compound from the reaction bath; and carrying out an oil-in-water type microencapsulation selected from the group consisting of an interfacial polymerization method and an in-situ polymerization method which comprises dispersing water-insoluble or slightly soluble capsaicine compound in water and forming polymer walls, which are insoluble in core materials containing the capsaicine compound and Water, on the surface of the dispersed particles.

4. The princess of claim 3, wherein said condensing step is carried out in the presence of an acid binding agent.

* * * * *